(12) United States Patent
Barlow

(10) Patent No.: US 11,555,800 B2
(45) Date of Patent: Jan. 17, 2023

(54) MONITOR AND INDICATOR SYSTEM

(71) Applicant: David George Barlow, Jackson, WY (US)

(72) Inventor: David George Barlow, Jackson, WY (US)

( * ) Notice: Subject to any disclaimer, the term of this patent is extended or adjusted under 35 U.S.C. 154(b) by 0 days.

(21) Appl. No.: 16/990,997

(22) Filed: Aug. 11, 2020

(65) Prior Publication Data

US 2021/0048409 A1 Feb. 18, 2021

Related U.S. Application Data

(60) Provisional application No. 62/885,646, filed on Aug. 12, 2019.

(51) Int. Cl.
*G01N 27/416* (2006.01)
*G01N 27/30* (2006.01)

(52) U.S. Cl.
CPC ....... *G01N 27/4166* (2013.01); *G01N 27/307* (2013.01)

(58) Field of Classification Search
CPC ............. G01N 27/307; G01N 27/4166; G01N 27/4168; G01N 33/182
See application file for complete search history.

(56) References Cited

U.S. PATENT DOCUMENTS

| | | | |
|---|---|---|---|
| 4,802,255 A | 2/1989 | Breuer et al. | |
| 4,872,235 A | 10/1989 | Nielsen | |
| 5,218,304 A * | 6/1993 | Kinlen | G01N 27/4166 204/412 |
| 5,683,655 A | 11/1997 | Carter | |
| 6,794,318 B2 | 9/2004 | Anderson et al. | |
| 8,481,470 B2 | 7/2013 | Jones, Jr. | |
| 8,518,704 B2 | 8/2013 | Campbell et al. | |
| 9,347,906 B2 | 5/2016 | Gruden | |
| 9,492,058 B2 | 11/2016 | Albright | |
| 9,510,668 B2 | 12/2016 | Patel et al. | |
| 9,829,471 B2 | 11/2017 | Hammond et al. | |
| 2003/0059483 A1 * | 3/2003 | Sowle | C11D 3/3955 424/661 |
| 2003/0211011 A1 | 11/2003 | Phillips et al. | |
| 2012/0145561 A1 * | 6/2012 | Coulon | G01N 33/1886 205/778.5 |
| 2013/0005048 A1 | 1/2013 | Felton et al. | |
| 2013/0065257 A1 | 3/2013 | Wang | |
| 2013/0214797 A1 | 8/2013 | Gruden | |

(Continued)

FOREIGN PATENT DOCUMENTS

WO 2017184664 A1 10/2017

OTHER PUBLICATIONS

International Search Report and Written Opinion dated Dec. 7, 2020 issued in PCT Application No. PCT/US2020/045825.

*Primary Examiner* — Gurpreet Kaur
(74) *Attorney, Agent, or Firm* — Avek IP, LLC

(57) ABSTRACT

A monitor and indicator system includes a sensor part, a control and indication part, and a power part. The monitor and indicator system is configured to: (a) monitor a concentration of a sterilant in a sanitizing solution; (b) determine a depletion of the sterilant upon detecting that the concentration of the sterilant becomes equal to or falls below a predetermined threshold concentration level; and (c) indicate the depletion of the sterilant of the sanitizing solution by emitting a notification.

10 Claims, 7 Drawing Sheets

(56) References Cited

U.S. PATENT DOCUMENTS

| | | |
|---|---|---|
| 2015/0115983 A1 | 4/2015 | Potyrailo et al. |
| 2015/0352210 A1* | 12/2015 | Wang .................. B01J 2/02 |
| | | 424/400 |
| 2015/0374868 A1 | 12/2015 | Bruce et al. |
| 2016/0116418 A1 | 4/2016 | Clark |
| 2017/0007731 A1 | 1/2017 | Sharma |

* cited by examiner

MONITOR AND INDICATOR SYSTEM

CROSS-REFERENCE TO RELATED APPLICATIONS

This application claims the benefit of priority of U.S. Provisional Patent Application No. 62/885,646, filed Aug. 12, 2019, the disclosure of which is incorporated by reference herein in its entirety.

FIELD OF THE DISCLOSURE

The disclosure relates generally to the field of sanitization monitoring and indication. More specifically, the disclosure relates to the field of a monitor and indicator system for sanitization systems.

BACKGROUND

Sanitization systems are used to reduce the presence of microorganisms on a surface. Cross-contamination can occur not just when a utensil contacts multiple food sources but can also occur when the utensil touches a common allergen, such as nuts. Additionally, microorganism growth can occur when utensils are improperly cleaned, or are not cleaned in a timely manner which may cause adverse effects to the public. Food surfaces that contact food that has not been prepared or refrigerated properly can contaminate other food, causing harmful effects if ingested. Thus, maintaining clean and sanitized food contact surfaces, such as knives and other utensils, is an integral part of the food service industry.

Different chemical substances may be utilized as sanitizing agents in sanitizing solutions. Commonly used chemical substances include chlorine (bleach), quaternary ammonium, iodine, and others. Sanitizing solutions with one or more of these chemical substances must be changed regularly in sanitization processes because the concentration of these chemical substances decreases over time, thus eventually losing the sanitizing effects. Therefore, laws, regulations, or policies usually requires the concentration of the sanitizing chemical substances to be within certain ranges to assure the desired sanitization effects. For example, a chlorine sanitizing solution is usually required to have a concentration of 50 to 200 parts per million (ppm) chlorine; a quaternary ammonium sanitizing solution is usually required to have a concentration of 100 to 400 ppm quaternary ammonium; and an iodine sanitizing solution is usually required to have a concentration of 5 to 50 ppm iodine.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

According to one embodiment of the invention, a monitor and indicator system includes a sensor part, a control and indication part, and a power part. The monitor and indicator system is configured to: (a) monitor a concentration of a sterilant in a sanitizing solution; (b) determine a depletion of the sterilant upon detecting that the concentration of the sterilant becomes equal to or falls below a predetermined threshold concentration level; and (c) indicate the depletion of the sterilant of the sanitizing solution by emitting a notification.

According to another embodiment of the invention, a method for monitoring a concentration of a sanitizing chemical substance in a sanitizing solution includes: (a) providing a container; (b) filling the container with a sanitizing solution comprising a sterilant; (c) placing a monitor and indicator system having a sensor part, a control and indication part, and a power part in the container; (d) activating the monitor and indicator system to measure a concentration of the sterilant; (e) activating the monitor and indicator system to emit a first notification when a measured concentration of the sterilant in the sanitizing solution is above a predetermined threshold concentration level; (f) activating the monitor and indicator system to emit a second notification to indicate a depleted sanitizing solution when the measured concentration of the sterilant in the sanitizing solution becomes equal to or falls below the predetermined threshold concentration level; (g) replacing the depleted sanitizing solution with a new batch of sanitizing solution having a concentration of the sterilant above the predetermined threshold concentration level; (h) disposing the monitor and indicator system; and (i) placing a new monitor and indicator system in the kitchen container with the new batch of sanitizing solution.

BRIEF DESCRIPTION OF THE DRAWINGS

Illustrative embodiments of the invention are described in detail below with reference to the attached figures.

DETAILED DESCRIPTION

All states have food services codes and regulations that prescribe acceptable methods and times for cleaning utensils (e.g., knives, spoons, forks, etc.) The regulations usually require the concentration of the sanitizing chemical substances to be within certain ranges to assure the desired sanitization effects. However, maintaining this appropriate level of cleanliness relies on the dedication and common sense of those persons responsible for ensuring that the codes and regulations are being complied with. For example, while a chlorine sanitizing solution is very effective in killing bacteria and other microbes and preventing contamination in food industries, the chlorine concentration of the solution decreases over time, thus losing the sanitizing effects after being exposed to materials such as food waste. If no one is checking the concentration of the solution, then the solution may not be effective to sanitize the utensils.

Depending on the foodstuffs that the utensil contacts, the utensil may need to be cleansed very frequently with a sanitizing solution. Thus, sanitation processes can often be laborious and time intensive, and the sanitizing solutions may be depleted quickly, which is especially inconvenient during high service periods, such as lunch and dinner. In some cases, food industry personnel may not always be able to timely use traditional chlorine test strips to measure the chlorine concentration of the chlorine sanitizing solutions, and thus may not be able to timely replace depleted chlorine sanitizing solutions. Accordingly, it may be desirable to have a simple, automatic, reliable, and low-cost monitor and indicator system to better remind the food industry personnel and notify them of the depleted chlorine sanitizing solutions which need to be replaced.

Figure 1:
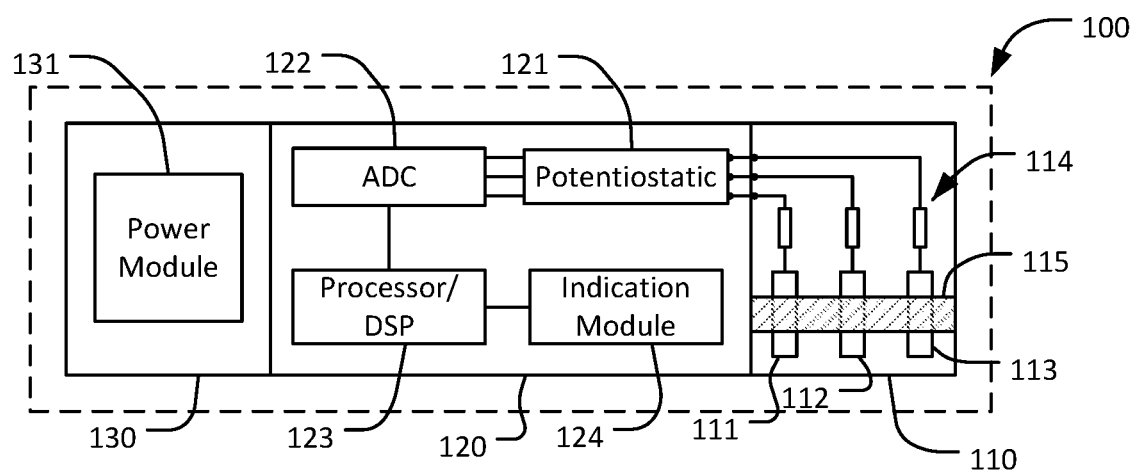
FIG. 1 shows an embodiment of a monitor and indicator system.

Systems and methods for monitoring the efficacy of sanitizing solutions are illustrated in FIGS. 1-7. Referring first to FIG. 1, in some embodiments, a monitor and indicator system 100 may generally include a sensor part 110, a control and indication part 120, and a power part 130. The sensor part 110 may include a disposable screen-printed electrode system, which can be a multi-electrode system such as a two-electrode system, a three-electrode system, a four-electrode system, et cetera. In the three-electrode system shown in FIG. 1, the disposable screen-printed electrode system may include a counter electrode 110, a working electrode 120, and a reference electrode 130. The sensor part 110 may be covered (or laminated in some embodiments) with a top insulation layer 114 having an opening 115 to concurrently expose parts of the counter electrode 110, working electrode 120, and reference electrode 130 while sealing off the remaining parts of the sensor part 110 from the external environment (e.g., gas, liquid, solid). The control and indication part 120 may include a potentiostatic module 121, an analog/digital converter module 122, a processor module 123, and an indication module 124. The power part 130 may include a power module 131.

As will be described in greater detail below, in embodiments, the sensor part 110, the control and indication part 120, and the power part 130 may be manufactured separately and configured to be connected together. One or more of the parts 110, 120, and/or 130 may be configured as a sticker which may be disposed on the side of a container. In other embodiments, the various parts 110, 120, and 130 may be manufactured together as a single disposable and configurable monitor and indicator system 100, which may, but need not be, a sticker.

In any event, a user may place the system 100 inside of a vessel having the sanitizing solution therein. The concentration of the sanitizing solution will gradually decrease over time with use. The sensor part 110 may determine the concentration of the sanitizing agent (e.g., chlorine) in the sanitizing solution in real time as described herein. When the indication module 124 is activated, a user knows that the concentration of a sanitizing solution is below the lower limit, and it is time to replace the depleted sanitizing solution with a new batch of sanitizing solution having a concentration of the sanitizing chemical substance above the predetermined threshold concentration level. If the system 100 is disposable, a new sticker 100 may be disposed into the new batch of the sanitizing solution, or the disposable portion of the system 100 may be replaced.

Figure 2:
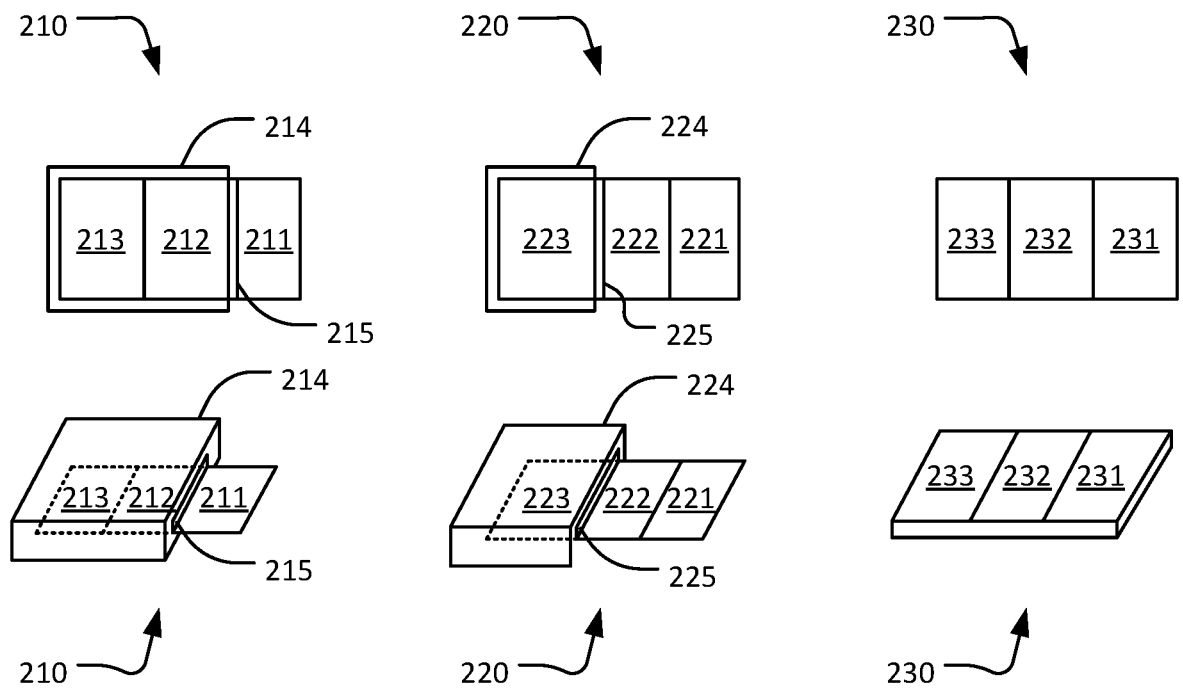
FIG. 2 shows exemplary embodiments of monitor and indicator systems.

FIG. 2 shows the monitor and indicator system 100 according to various embodiments. In embodiment 210, the control and indication part 212, and the power part 213 of the monitor and indicator system 100 may be enclosed within an external housing 214 configured to connect to the sensor part 211 of the monitor and indicator system 100 by a connection socket 215. In this embodiment 210, the sensor part 211 of the monitor and indicator system 100 may be disposable, and may be replaced after a single test, multiple tests, or a period of predetermined testing time. The control and indication part 212 and the power part 213 enclosed within the external housing 214 may be either disposable or permanent. And in some embodiments, this external housing 214 may be free or fixed inside or outside a sanitizing solution.

In embodiment 220, the sensor part 221 and the control and indication part 222 of the monitor and indicator system 100 may be manufactured together as an integral disposable piece which may be replaced after a single test, multiple tests, or a period of predetermined testing time. This disposable piece including the sensor part 221 and the control and indication part 222 may be connected to the power part 223 by a connection socket 225. The power part 223 of the monitor and indicator system 100 may be enclosed in an external housing 224. And in some embodiments, this external housing 224 may be free or fixed inside or outside a sanitizing solution.

In embodiment 230, the sensor part 231, the control and indication part 232, and the power part 233 may be altogether manufactured as an integral single piece, and act as a disposable monitor and indicator system 100 which may be a sticker and may be disposed after a single test, multiple tests, or a period of predetermined testing time. As with embodiments 210 and 220, in embodiment 230, the disposable monitor and indicator system 100 may be free or fixed inside or outside a sanitizing solution.

While only three embodiments 210, 220, and 230 of the monitor and indicator system 100 are shown in FIG. 2, it is to be understood that the sensor part 231, the control and indication part 232, and the power part 233 of the monitor and indicator system 100 may be individually or in combination manufactured as disposable or permanent pieces. In addition, they may also individually or in combination function as disposable or permanent pieces.

Figure 3:
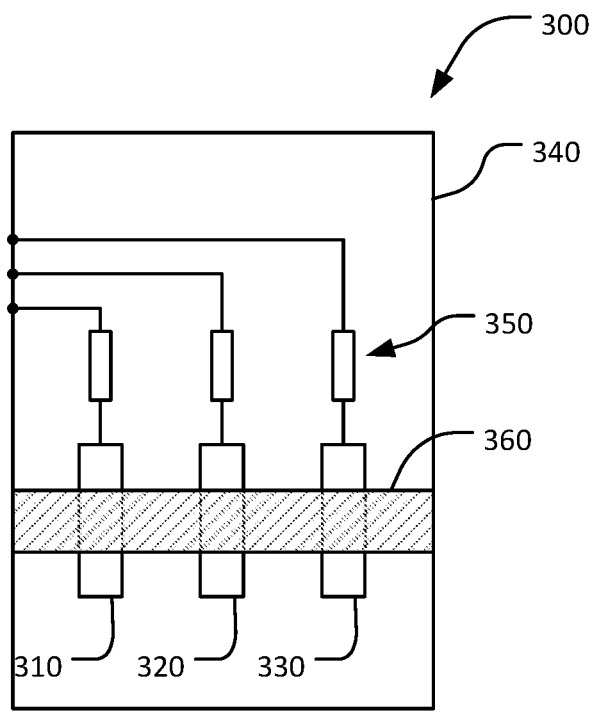
FIG. 3 shows an exemplary embodiment of a disposable screen-printed electrode.

Moving on, FIG. 3 shows a disposable screen-printed electrode 300 which may individually or in combination function as the sensor part 110 of the monitor and indicator system 100. A disposable screen-printed electrode 300 may include a counter electrode 310, a working electrode 320, and a reference electrode 330. These electrodes may be individually or in combination made of materials such as platinum, palladium, gold, silver, silver chloride, potassium chloride, nickel, aluminum, calcium, cesium, bromine, lithium, molybdenum, copper, zinc, cobalt, brass, titanium, thorium, zirconium, lanthanum, cerium, ruthenium, iridium, manganese, cadmium, indium tin oxide, graphite, graphene, carbon, lead, pencil lead, ceramic, plastics, polymers, nanotubes, nanowires, nanorods, boron-doped diamond, diamond, ferrocene, benzethonium chloride, and mixed metal oxides including oxides of precious metals ruthenium, iridium, platinum, and titanium.

The disposable screen-printed electrode 300 may further include a substrate film 340 on which the counter electrode 310, the working electrode 320, and the reference electrode 330 are disposed. The substrate film 340 may be individually or in combination made of materials such as glass, aluminum, ceramic, metal, paper, wax, silicon, silicon carbide, polyester, cyclic olefin copolymer, polyethylene, polyethylene terephthalate, polypropylene, polystyrene, polyvinyl chloride, polyvinylidene chloride, polyvinylidene difluoride, polyamide, polyimide, polychlorotrifluoroethylene, polycarbonate, polyurethane, acrylonitrile butadiene styrene, polyacetylene, polytetrafluoroethylene, phenolics, polyimide, polysulfone, polypyrrole, para-aramid, polychloroprene, polyaniline, polythiophene, polyvinylpyrrolidone, polystyrenesulfonate, polyacrylonitrile, phenol-formaldehyde resin, furan, silicone, polymethylmethacrylate, ethyl cellulose, polyether ether ketone, polyethylene naphthalate, and other suitable polymeric materials. In some embodiments, the substrate film may be a rigid or flexible tape. Preferably, the substrate film 340 is configured to survive in temperatures ranging from about −20° C. (−4° F.) to about 150° C. (302° F.).

An insulation layer 350 with an opening 360 may be provided on top of the substrate film 340, covering the electrodes 310, 320, and 330. While the opening 340 of the insulation layer 350 shown in FIG. 3 has a rectangular configuration, it is to be understood that this opening 340 may be in any shape so long as it concurrently exposes parts of the counter electrode 310, working electrode 320, and reference electrode 330 while sealing off the remaining parts of the disposable screen-printed electrode 300 from the external environment (e.g., gas, liquid, solid).

Figure 4:
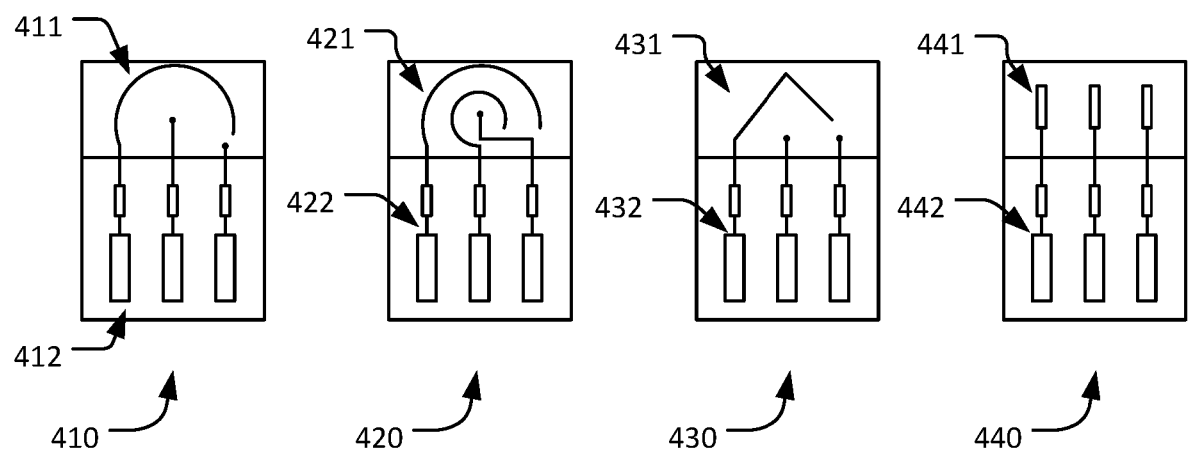
FIG. 4 shows embodiments of disposable screen-printed electrodes.

FIG. 4 shows some further exemplary embodiments 410, 420, 430, and 440 of the disposable screen-printed electrode 110. The screen-printed electrodes in embodiments 410, 420, 430, and 440 all include three-electrodes each having its own arrangement of electrode shapes.

The electrodes may be configured to measure voltage and current within the solution. Depending on the results, it may be possible to determine whether the solution is within an acceptable range, and therefore, whether the solution needs to be changed.

In embodiments, the screen-printed electrode 110 may be replaced with a chemically sensitive field-effect transistor (ChemFET). The ChemFET may be used as a sensor for measuring chemical concentration of the sanitizing solution. As the chemical concentration of the sanitizing solution changes, the current through the transistor changes accordingly.

Figure 5:
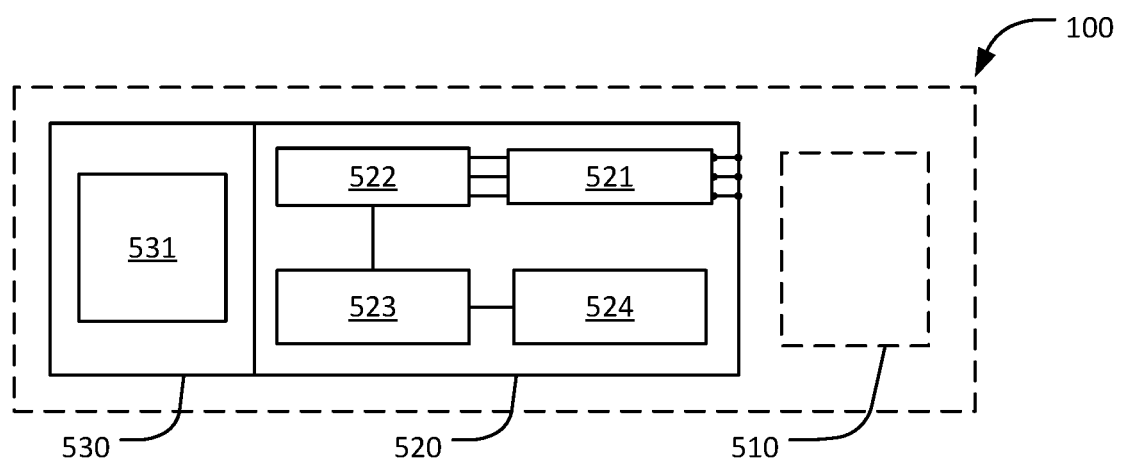
FIG. 5 shows an exemplary embodiment of a power part and a control and indication part of a monitor and indicator system.
Figure 6A:
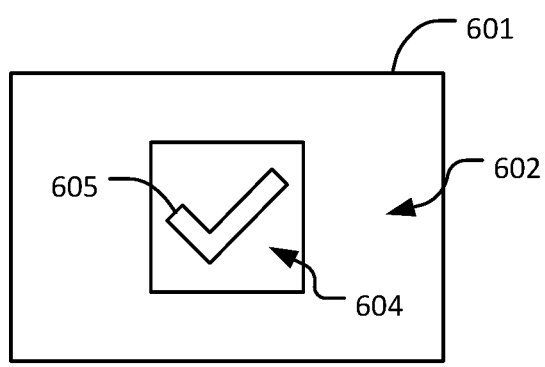
FIG. 6A shows an embodiment of a monitor and indicator system with various external indication functions.
Figure 6B:
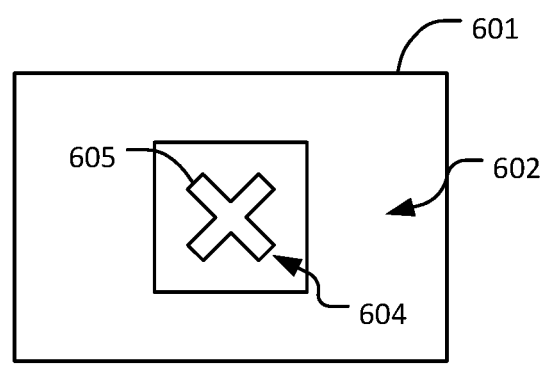
FIG. 6B shows another embodiment of a monitor and indicator system with various external indication functions.

FIG. 5 illustrates an embodiment of the control and indication part 520 (corresponding generally to the control and indication part 120 in FIG. 1) and the power part 530 (corresponding generally to the power part 130) of a monitor and indicator system 100. The control and indication part 520 may include a potentiostatic module 521, an analog/digital converter module 522, a processor module 523, and an indication module 524. In some embodiments, the potentiostatic module 521 may receive electrochemical signals from the disposable screen-printed electrode in a sensor part 510 (corresponding generally to the sensor part 110, and also described as embodiments 300, 410, 420, 430, and 440). And the potentiostatic module 521 may be in further electrical connection with the processor 523 via an analog-digital converter 522. The analog digital converter 522 may convert the analog signals received from the potentiostatic module 521 to digital signals, and then send the converted digital signals to the processor 523. Depending on the received digital signals from the analog-digital converter 522, the processor 523 may decide if the measured concentration of the sanitizing solution is above a target range, within the target range, or below the target range, and then actuate the indication module 520 accordingly based on the concentration measurements, as will be described in greater detail below. The processor 523 may cause the indication module 524 to (1) activate a low power lighting source 605 (examples shown in FIGS. 6A & 6B) to provide one or more alert notification(s) to a user; (2) activate a transmission module within it to transmit one or more alert notification(s) wirelessly or by-wire to a remote device; (3) activate a mechanical mechanism within it to release a notification dye of a specific color; and/or (4) activate a speaker to play a notification message, for example. The power part 530 of the monitor and indicator system 100 may include a power module 531 which can be a battery (which may be configured to have a certain predefined shelf-life), an internal electrochemical source powered by chemical energy or electrochemical energy, a power interface in wired or wireless connection with an external power source, or any other means of providing the necessary power to the system, whether now known or later developed.

In some embodiments, the indication module 524 may include one or more low power lighting source such as an ultra-low power light-emitting diode (LED), a low-power lamp, a low-power light bulb, or a low-power luminescent light source. In an example, the indication module may include one or more red ultra-low power LED units which can be activated when the concentration of the sanitizing solution is equal to or falls below a predetermined concentration threshold level. The indication module 524 may further include one or more green ultra-low power LED units which can be activated when the concentration of the sanitizing solution is above a predetermined concentration threshold level.

In other embodiments, the indication module 524 may include a transmission module configured to transmit an alert notification (e.g., wirelessly) to a remote device. In an example, the indication module 524 may be activated to transmit a wireless notification to a remote device when the concentration of the sanitizing solution becomes equal to or falls below a predetermined concentration threshold level. Optionally, the indication module 524 may transmit notifications at predetermined intervals indicating the real-time chlorine concentration of the chlorine sanitizing solution or merely notifications that the concentration is above/below the threshold to a remote device. Optionally, the notifications may be exact concentrations.

In further embodiments, the indication module 524 may include a mechanical mechanism to release a dye into the sanitizing solution. Depending on different applications, a single dye or a combination of multiple dyes may be used. For example, a non-reactive food dye may be released and dissolved in the sanitizing solution when the concentration becomes equal to or falls below a predetermined concentration threshold level. A user can therefore easily detect that the sanitizing solution is depleted and needs to be replaced.

In another embodiment, a non-reactive dye may be released in the monitor and indicator system 100, instead of being released and dissolved into the sanitizing solution. Of course, both reactive and non-reactive dyes may be used individually or in combination.

While the above embodiments illustrate some specific configurations of the monitor and indicator system 100, it is to be understood that there may be other configurations which may be capable of implementing similar functions and/or achieving similar results. For example, it should be understood that in some embodiments, the control and indication part 520 (generally 120) and the power part 530 (generally 130) may be manufactured together, enclosed within an external housing, and in connection with the sensor part 510 (generally 110) of the monitor and indicator system 100 by a connection socket. In this case, the sensor part 510 of the monitor and indicator system 100 may be disposable, and it may be replaced after a single test, multiple tests, or a period of predetermined testing time. The control and indication part 520 and the power part 530 enclosed within the external housing may be either disposable or permanent. A user may thus replace the sensor part 510 upon replacing a depleted solution with a new batch of solution without throwing away the external housing enclosing the control and indication part 520 and the power part 530. In other embodiments, the control and indication part 520 and the sensor part 510 may be manufactured together as the disposable portion in connection with the power part 530 via a connection socket. And the power part 530 may be on its own enclosed within another external housing. In this case, the user may replace the disposable portion containing the sensor part 510 and the control and indication part 520 each time when the depleted solution is replaced with a new batch of solution without throwing away the power part 530.

Moving on, FIG. 6 illustrates further embodiments of the monitor and indicator system 100 with various external indication functions to indicate the good and/or bad status of the sanitizing solution based on whether the measured concentration level of the sanitizing solution is above a predetermined concentration threshold level. As shown in FIG. 6, the monitor and indicator system 100 may include a substrate film layer 601 and an insulation layer 602. The insulation layer 602 may include a display area 604 configured to display a notification 605. In some examples, the display area 604 may be activated to display a check mark 605 when the concentration of the sanitizing solution is above a predetermined concentration threshold level. And the check mark may be of a color, such as green, which is easily recognizable as a color that indicates that the status is "good." In other examples, the display area 604 of the monitor and indicator system 100 may be activated to display a cross mark 605 when the concentration of the sanitizing solution becomes equal to or falls below a predetermined concentration threshold level. And the cross mark may be of a color, such as red, which is easily recognizable as a color that indicates that the status is "bad."

Figure 7:
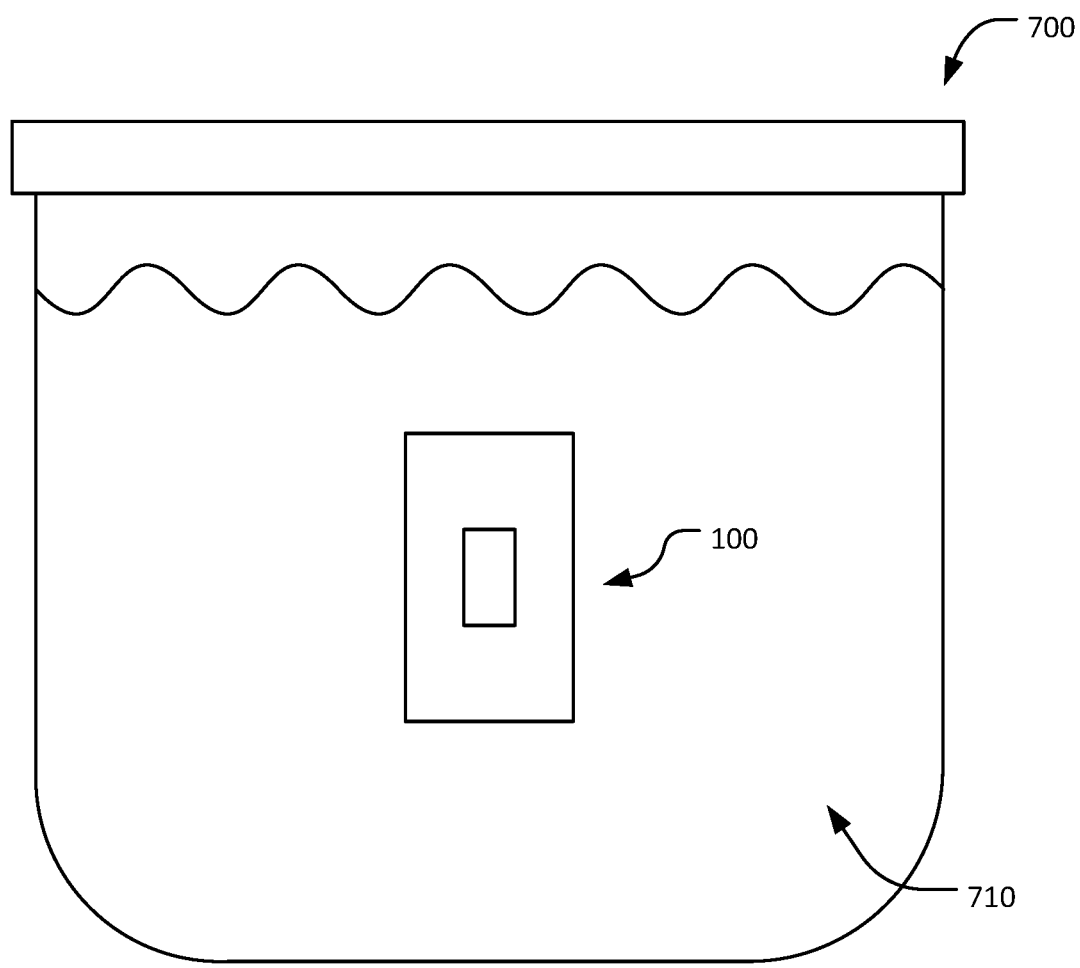
FIG. 7 shows an embodiment of a kitchen item with a monitor and indicator system.

FIG. 7 illustrates a sanitizer monitor 100 in use. Here, a container 700 may be filled with a sanitizing solution 710 and positioned near a food processing site. The sanitizing solution 710 may be used to sanitize kitchen utensils after use. A user may dispose a monitor and indicator system 100 (which may be a sticker) within the kitchen container 700 freely or in a fixed position. The monitor and indicator system 100 may immediately start working upon being in contact with the sanitizing solution (e.g., which may be powered by the electrical charges from the sanitizing solution). The monitor and indicator system 100 may continuously measure the concentration of the sanitizing compound element in the sanitizing solution 710 as described above. When the concentration of the sanitizing solution is above the predetermined concentration threshold, the monitor and indicator system 100 may activate the indication module 124 to emit a first notification (e.g., light indication, wired or wireless signal, dye, sound, etc.), or the system 100 may remain otherwise dormant. When the concentration of the sanitizing solution becomes equal to or falls below the predetermined concentration threshold, the monitor and indicator system 100 activates the indication module 124 to emit a second notification (e.g., light indication, wired or wireless signal, dye, sound, etc.) indicating that the sanitizing solution needs to be change. The kitchen personnel will see the notification, and subsequently replace the depleted sanitizing solution with a new batch of sanitizing solution having a concentration of the sanitizing chemical substance above the predetermined threshold concentration level. The kitchen personnel may dispose the used sticker monitor and indicator system 100 (or dispose a portion of the system 100 thereof, as the case may be) and insert a new monitor and indicator system 100 into the container 700.

In embodiments, a method for maintaining a concentration of a sanitizing solution may include the following steps: (a) providing a container; (b) filling the container with a sanitizing solution comprising a sanitizing chemical substance; (c) placing a first monitor and indicator system in or on the container, wherein the system has an adhesive area; (d) activating the monitor and indicator system to measure a concentration of the sanitizing chemical substance; and (e) activating the monitor and indicator system to emit a notification when the measured concentration of at least one sanitizing chemical substance is above a predetermined threshold concentration level, thus indicating a depleted sanitizing solution. The method may further include (f) replacing the depleted sanitizing solution with a new batch of sanitizing solution having a concentration of the sanitizing chemical substance above the predetermined threshold concentration level; (g) disposing of the first monitor and indicator system; and (i) placing a second monitor and indicator system on a surface of the kitchen container.

In other embodiments, a method for monitoring and indicating a concentration of a sanitizing solution may include the following steps: (a) providing a container; (b) filling the container with a sanitizing solution comprising a sanitizing chemical substance; (c) placing a monitor and indicator system with a sensor part, a control and indication part, and a power part in the container with the sanitizing solution; (d) activating the monitor and indicator system to measure a concentration of the sanitizing chemical substance; (e) activating the monitor and indicator system to emit a first notification when the measured concentration of the sanitizing chemical substance is above a predetermined threshold concentration level; (f) activating the monitor and indicator system to emit a second notification when the measured concentration of the sanitizing chemical substance becomes equal to or falls below a predetermined threshold concentration level, thus indicating a depleted sanitizing solution; (g) replacing the depleted sanitizing solution with a new batch of sanitizing solution having a concentration of the sanitizing chemical substance above the predetermined threshold concentration level; (h) disposing the monitor and indicator system; and (i) placing a new monitor and indicator system in the kitchen container with the new batch of sanitizing solution freely or in a fixed position.

In further embodiments, a method for monitoring and indicating a concentration of a sanitizing solution may include the following steps: (a) providing a container; (b) filling the container with a sanitizing solution comprising a sanitizing chemical substance; (c) providing a housing with a power part (e.g., battery) of a monitor indicator system including a sensor part and a control and indication part in the container with the sanitizing solution, wherein the parts are separable and the sensor part is disposable; (d) placing the housing with the power part in the container with the sanitizing solution freely or in a fixed position; (e) connecting the disposable sensor part and control and indication part of the monitor and indicator system to the housing by a connection socket; (e) activating the monitor and indicator system to measure a concentration of the sanitizing chemical substance; (f) activating the monitor and indicator system to emit a first notification when the measured concentration of the sanitizing chemical substance is above a predetermined threshold concentration level; (g) activating the monitor and indicator system to emit a second notification when the measured concentration of sanitizing chemical substance becomes equal to or falls below a predetermined threshold concentration level, thus indicating a depleted sanitizing solution; (h) replacing the depleted sanitizing solution with a new batch of sanitizing solution having a concentration of the sanitizing chemical substance above the predetermined threshold concentration level; (i) disposing the sensor part and control and indication part of the monitor and indicator system; and (j) connecting a new sensor part and a new control and indication part of the monitor and indicator system to the housing with the power part in the container with the new batch of sanitizing solution via the connection socket.

In embodiments, the monitor and indicator system 100 may be particularly useful in the food industries to monitor and/or indicate the concentration of a sanitizing chemical substance in a sanitizing solution for cleaning kitchen utensils, and to optionally send notifications when the concentration of the sanitizing compound element becomes equal to or falls below a predetermined level as described herein. For example, the sanitizing solution may be used to clean and sanitize surfaces that come into contact with food, such as knives, spoons, forks, and other utensils.

The sterilant may be one or more of the following chemicals: alcohol, formalin, glutaraldehyde, hydrogen peroxide, ozone, potassium permanganate, peroxyacid, phenolics, quaternary ammonium compounds, chlorine, hypo chlorite, hypochlorous acid, iodine, iodophors, sodium hydroxide, potassium hydroxide, calcium hydroxide, magnesium hydroxide, sulfurous acid, sulfur dioxide, thymol, pine oil, lactic acid, sodium bicarbonate, polyaminopropyl biguanide, diethylene glycol, benzethonium chloride, et cetera.

The monitor and indicator system 100 may be used to test, monitor, and/or indicate a chlorine concentration of a chlorine sanitizing solution, which may be prepared by adding chlorine or one or more chlorine compounds (e.g., sodium hypochlorite) to water. And the chlorine concentration may range from 10 to 200 ppm. Preferably, the upper chlorine concentration limit may be 200 ppm and the lower chlorine concentration limit may be 50 ppm. The threshold chlorine concentration may be set to between 10 and 200 ppm, and in embodiments, may be, for example, 50 ppm, 75 ppm, 100 ppm, 125 ppm, 150 ppm, or 175 ppm.

In embodiments, the monitor and indicator system 100 is used to test, monitor, and/or indicate a quaternary ammonium concentration of a quaternary ammonium sanitizing solution. And the quaternary ammonium concentration may range from 100 to 400 ppm. In embodiments, the upper quaternary ammonium concentration limit may be 200 ppm and the lower quaternary ammonium concentration limit may be 150 ppm. The threshold quaternary ammonium concentration may be set to between 100 and 400 ppm, and in embodiments, may be, for example, 100 ppm, 125 ppm, 150 ppm, 175 ppm, 200 ppm, 225 ppm, 250 ppm, 275 ppm, 300 ppm, 325 ppm, 350 ppm, 375 ppm, or 400 ppm.

In other embodiments, the monitor and indicator system 100 is used to test, monitor, and/or indicate an iodine concentration of an iodine sanitizing solution. And the iodine concentration may range from 5 to 50 ppm. In embodiments, the upper iodine concentration limit may be 25 ppm while the lower iodine concentration limit may be 12.5 ppm. The threshold iodine concentration may be set to between 5 and 50 ppm, and in embodiments, may be, for example, 5 ppm, 10 ppm, 15 ppm, 20 ppm, 25 ppm, 30 ppm, 35 ppm, 40 ppm, 45 ppm or 50 ppm.

As described briefly above, the monitor and indicator system may be a sticker having a generally rectangular shape. The length of the monitor and indicator sticker system may be 1 to 10 inches; the width of the monitor and indicator sticker system may be 0.5 to 5 inches, for example; and the depth of the monitor and indicator sticker system may be 0.1 to 5 inches, for example. In an exemplary embodiment, the length of the monitor and indicator sticker system may be 2 to 3 inches, and the width of the monitor and indicator system may be about 1 inch. Other shapes and configurations of the sticker are also contemplated within the scope of the invention.

EXAMPLES

Active chlorine is difficult to measure at high levels (e.g., greater than 50 ppm). Test strips are known to be inaccurate, and alternative methods of monitoring chlorine levels, such as ion-specific electrodes, are expensive and subject to contamination-induced errors. An experiment was designed to test active chlorine levels in a solution that contains chlorine bleach from sodium hypochlorite solutions or organic chlorine sources (e.g., sodium dichloroisocyanurate). Hypochlorite is a strong oxidizer; accordingly, the electrical properties of the solution were studied.

Electrodes (Cu cathode, Zn anode) were placed in a sanitizer solution containing an active chlorine source. The theoretical potential for the Cu/Zn electrode couple is 1.10 volts direct current (VDC). In the solution, the electrode a measured voltage of 0.95 volts direct current (VDC) and a current of about 15-20 mAmps. Without an active chlorine source, such as sodium dichloroisocyanurate, the measured voltage of the solution is approximately equal to the solution with the active chlorine source; however, the current produced is significantly lower, measuring at below 2 mAmps. The low current produced in the non-active chlorine solution is likely due to the reaction of the Zn anode with the alkaline solution, which likely forms zinc hydroxide. In the active chlorine solution, the higher levels of current measured is believed to be due to oxidation of the zinc anode by the sodium hypochlorite. Although the concentration of the sodium hypochlorite was not specifically measured, the current produced due to the oxidation fo the Zn is proportional to the hypochlorite concentration. Similarly, the amount of current produced is proportional to the surface area of the anode.

Several experiments were conducted for various solution compositions. Distilled water having a pH of between 6.2 and 6.8 was used in all measurements. Measurements were taken at room temperature, ranging from about 18.5-19.5 degrees Celsius. The measured voltage of the distilled water ranged from 0.85 to 0.9 VDC, with no current measured. The surface area of the electrodes was about 6 square inches. The base solution is a propriety sanitizing solution manufactured by Purdy®, and contains all sanitizing components except sodium dichloroisocyanurate. The sodium dichloroisocyanurate was procured from Purdy for addition to the test solutions. The pH of the base solution was 10.5 to 11.0. After addition of the chlorine source, the pH of the solution was reduced about ½ to 1 pH unit.

Without the chlorine source, the sanitizing solution had a pH of about 11.0. the measured voltage was 0.95 VDC and the measured current was 0.5 to 1.5 mAmp. With the chlorine source, the sanitizing solution had a pH of 10.5, the measured voltage was 0.94 VDC, and the measured current was 18 mAmp+1-2 mAmp. The measured current was observed to be somewhat unstable unless the solution was stirred.

Addition of the chlorin source to the base solution provided noticeable changes in the measured current which appears to be proportional to the amount of the chlorine source added. In several instances, it was observed that the measured current was nearly double when the amount of chlorine doubled.

The electrodes may experience polarization over time. In a static system without agitation, a charged layer of ions may build up at the surface of the electrodes. This may inhibit diffusion of the reactants thereby slowing the reaction at the surface of the electrodes causing inaccurate readings. To create a dynamic system, a magnetic stirrer was used to maintain agitation in the system which appeared to minimize the effect of polarization and allow stable current readings.

In addition to polarization, contamination of the surface of the anode (Zn) with reaction products (e.g., ZnO) may occur. The contamination was observed as a buildup of white precipitate on the surface of the anode.

Hypochlorite in the solution is consumed at the anode. This reaction produces the current used to determine the hypochlorite concentration. It is believed that there is not enough hypochlorite consumed to interfere with the overall performance of the system. This is because, in the system, there is equilibrium among the parent compound (sodium dichloroisocyanurate) and the various species of hypochlorite compounds. As hypochlorite is consumed at the anode, more is "released" by the sodium dichloroisocyanurate. This equilibrium helps to maintain the level of hypochlorite in the solution.

Surface contamination of the anode may result in a lower current reading. Contamination may be due to build of food stuffs in the solution (e.g., fats, oils, particulates). It is believed that by the time this buildup is significant enough to have an effect on the readings that it will be desirable by the user to change the solution based on the dirty nature of the water regardless of any reading.

Based on the observed results, it can be determined that the concentration of the hypochlorite in the solution may be indirectly followed via the current produced by a galvanic cell.

Many different arrangements of the various components depicted, as well as components not shown, are possible without departing from the spirit and scope of the present disclosure. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A monitor and indicator system, comprising:
a sensor; and
a control and indication part;
wherein:
the system is screen printed on a substrate film configured to survive temperatures ranging from −20 to 105 degrees Celsius;
the sensor comprises a disposable electrode system comprising an anode and a cathode;
the substrate film comprises an adhesive tape;
the control and indication part comprises a potentiostatic module, an analog/digital converter module, a processor module, and an indication module;
the potentiostatic module is configured to receive electrochemical signals from the sensor;
the analog/digital converter module is configured to convert analog signals received from the potentiostatic module to digital signals and to send the digital signals to the processor module; and
the processor module is configured to determine a depletion of a sterilant in a sanitizing solution upon detecting that a concentration of the sterilant becomes equal to or falls below a predetermined threshold concentration level and to actuate the indication module so that the indication module activates a mechanical mechanism within it to release a notification dye into the sanitizing solution.

2. The monitor and indicator system of claim 1, further comprising a power part, wherein the power part provides power for releasing the notification dye.

3. The monitor and indicator system of claim 1, wherein the system is screen printed on a substrate film configured to survive temperatures ranging from −20 to 150 degrees Celsius.

4. The monitor and indicator system of claim 3, wherein the substrate film comprises one or more of glass, aluminum, ceramic, metal, paper, wax, silicon, and silicon carbide.

5. The monitor and indicator system of claim 1, wherein:
the sensor comprises a disposable screen-printed two-electrode system, a disposable screen-printed three-electrode system, or a disposable screen-printed four-electrode system; and
each of the electrodes are made of one or more of platinum, palladium, gold, silver, nickel, aluminum, copper, zinc, brass, titanium, zirconium, ruthenium, iridium, graphite, graphene, carbon, and diamond.

6. A monitor and indicator system, comprising:
a sensor;
a control and indication part; and
a power part for providing power to the system, the power part comprising one or more of a battery, an internal electrochemical source powered by chemical energy or electrochemical energy, and a power interface in connection with an external power source;
wherein:
the control and indication part comprises a potentiostatic module, an analog/digital converter module, a processor module, and an indication module;
the potentiostatic module is configured to receive electrochemical signals from the sensor;
the analog/digital converter module is configured to convert analog signals received from the potentiostatic module to digital signals and to send the digital signals to the processor module; and
the processor module is configured to determine a depletion of a sterilant in a sanitizing solution upon detecting that a concentration of the sterilant becomes equal to or falls below a predetermined threshold concentration level and to actuate the indication module so that the indication module activates a mechanical mechanism within it to release a notification dye into the sanitizing solution.

7. The monitor and indicator system in claim 1, wherein the sterilant comprises chlorine.

8. The monitor and indicator system of claim 7, wherein the predetermined threshold concentration level of the sterilant in the sanitizing solution is 50 ppm.

9. The monitor and indicator system of claim 1, wherein the sterilant comprises quaternary ammonium, and the predetermined threshold concentration level of the quaternary ammonium in the sanitizing solution is 100 ppm.

10. The monitor and indicator system in claim 1, wherein the sterilant comprises iodine, and the predetermined threshold concentration level of the iodine in the sanitizing solution is 12.5 ppm.

\* \* \* \* \*